United States Patent [19]

Krieger

[11] Plant 4,575

[45] Jul. 15, 1980

[54] RHUBARB PLANT - K-1 VARIETY

[75] Inventor: Larry A. Krieger, Bridgman, Mich.

[73] Assignee: Stark Brothers Nurseries & Orchards Company, Louisiana, Mo.

[21] Appl. No.: 29,150

[22] Filed: Apr. 11, 1979

[51] Int. Cl.[2] ..... A01H 5/00
[52] U.S. Cl. ..... Plt./89
[58] Field of Search ..... Plt./89

*Primary Examiner*—Robert E. Bagwill
*Assistant Examiner*—James R. Feyrer
*Attorney, Agent, or Firm*—Burns, Doane, Swecker & Mathis

[57] ABSTRACT

A new and distinct variety of rhubarb plant is provided which originated as a mutation of the Valentine variety. This new variety is characterized by stalks of extremely large diameter, stalks which are red on both the inside and on the outside, tender stalks which cook-up well in the absence of strings and which require a substantially lesser quantity of sugar during processing, prominent leaf ribs, and the absence of seed stalks. This variety has been named the K-1 variety.

2 Drawing Figures

SUMMARY OF THE INVENTION

The rhubarb plant is recognized to be a herbaceous perennial, the underground portion of which consists of large, fleshy and somewhat woody rhizomes and a fibrous root system. The petioles or leaf stalks are used as food. A flower or seed stem commonly is formed in previously known varieties. The seeds produced from the pollinated flower will not reproduce true to form and consequently new plants intended for food production commonly are reproduced by division of the rhizomes.

The new and distinct variety of rhubarb plant originated as a rhizome mutation of a plant of the Valentine variety (non-patented) grown in a cultivated area among test plantings on property located on Skala Road in Baroda Township, Berrien County, Bridgman, Mich. This mutation was discovered by me in 1965 because of its distinctive characteristics, and has been continuously observed and tested by me from that date.

Rhubarb plants of the new variety possess:

(a) stalks of extremely large diameter, (b) stalks which are red on both the inside and on the outside, (c) tender stalks which cook-up well in the absence of strings and which require a substantially lesser quantity of sugar during processing, (d) prominent leaf ribs, and (e) the absence of seed stalks.

Asexual propagation of the new variety by division of rhizomes beginning in 1970 has demonstrated that its combination of characteristics comes true to form and is established and transmitted through succeeding generations. The specimens described herein were grown and observed at Bridgman, Mich.

BRIEF DESCRIPTION OF THE PHOTOGRAPHS

FIG. 1 illustrates typical rhubarb stalks of the K-1 variety (center) adjacent those of the Canada Red variety (left) and the McDonald variety (right). The stalks in each instance were pulled from the crown of the rhubarb plant, and accordingly the newly exposed surface at the base of each stalk which was formerly the point of attachment does not necessarily depict an accurate indication of the internal coloration of the stalk which would be apparent if the stalks were internally examined at another location. The external stalk colorations are depicted as nearly true as it is reasonably possible to make the same in a color illustration of this character.

FIG. 2 illustrates a typical leaf and stalk of the K-1 variety. The prominent leaf ribs of the new variety are apparent as is the unusually large stalk diameter, and the red internal coloration of the stalk. A Washington quarter placed upon the stalk gives for comparative purposes an indication of the stalk diameter. While every effort has been made to present an accurate color depiction, the reflection of light from the near surfaces of the stalk and veins tends to give an unnatural green appearance. The external surface of the stalk of the K-1 variety is in fact red as previously illustrated in FIG. 1.

DETAILED DESCRIPTION OF NEW VARIETY

Dates of first and last pickings: June 1 and September 15.

Overall plant: Large, strong, and vigorous, generally equal to the Valentine variety, and superior to the Canada Red, McDonald, and Victoria Giant varieties with respect to these characteristics. Stalks can readily be pulled or harvested without damage to plant over a long period of time. This variety lacks a seed stalk in all observations to date, and exhibits an extensive spreading root system.

Crown(third growing season):

*Very large.*—Approximately 18 to 24 inches in diameter, and solid. The crowns of the Valentine, Canada Red and McDonald varieties generally are approximately 15 to 20 inches in diameter and accordingly tend to be somewhat smaller than those of the present variety. The crown of the Victoria Giant variety tends to be large but is hollow in the middle.

Leaf:

*Size.*—Large, approximately 1 to 1½ feet in length. The leaf size is generally equivalent to that of the Valentine and McDonald varieties, and is larger than that of the Canada Red and Victoria Giant varieties.

*Shape.*—Ovate, cordate at base, margins entire but wavy.

*Veins.*—The leaf ribs are more prominent than those of the other varieties identified herein.

*Color.*—Greenish red with dark red veins. More red in leaves is exhibited than in the Canada Red variety. The Valentine variety possesses dark green leaves, while the McDonald and Victoria varieties possess light green leaves with green veins.

Leaf petiole (i.e. stalk):

*Size.*—Approximately 18 inches in length or about the same as the Valentine variety. The stalk diameter is approximately 1½ inches and exceeds that of other varieties. The maximum diameter of the stalk of the Valentine variety is approximately one inch. The stalk diameter is approximately twice that of the Canada Red variety.

*Texture.*—Medium fine and tender, cooks-up completely in a much shorter period of time than other varieties. Stalks of the Valentine and Canada Red varieties generally are superior to those of other varieties, but are not as fine and tender as those of the present variety. Stalks of the McDonald variety tend to be stringy, and those of the Victoria Giant tend to be tough and need to be peeled.

*Color.*—A complete very intense red, Carmine Red, Plate I-1-i of Ridgeway's Color Standards. Such red coloration tends to be deeper and more complete than that of other varieties discussed except the Canada Red variety. Also, the stalk of the McDonald variety tends to be green except near the crown. The intense red stalk coloration holds up well in the cooking process. Also, the internal coloration of the stalk is red, while that of the other varieties identified tends to be green or pink.

*Flavor.*—Mild and less acid than other varieties identified, excellent flavor. During processing approximately 50 percent less sugar is required than other varieties which tend by comparison to be sour and very acid.

*Storage.*—Stalks can be stored as long as those of the Valentine variety (i.e. the standard of quality).

*Use.*—All markets, local and distant.

I claim:

1. A new and distinct variety of rhubarb plant which is a mutation of the Valentine variety, substantially as illustrated and described, characterized by stalks of extremely large diameter, stalks which are red on both the inside and on the outside, tender stalks which cook-up well in the absence of strings and which require a substantially lesser quantity of sugar during processing, prominent leaf ribs, and the absence of seed stalks.

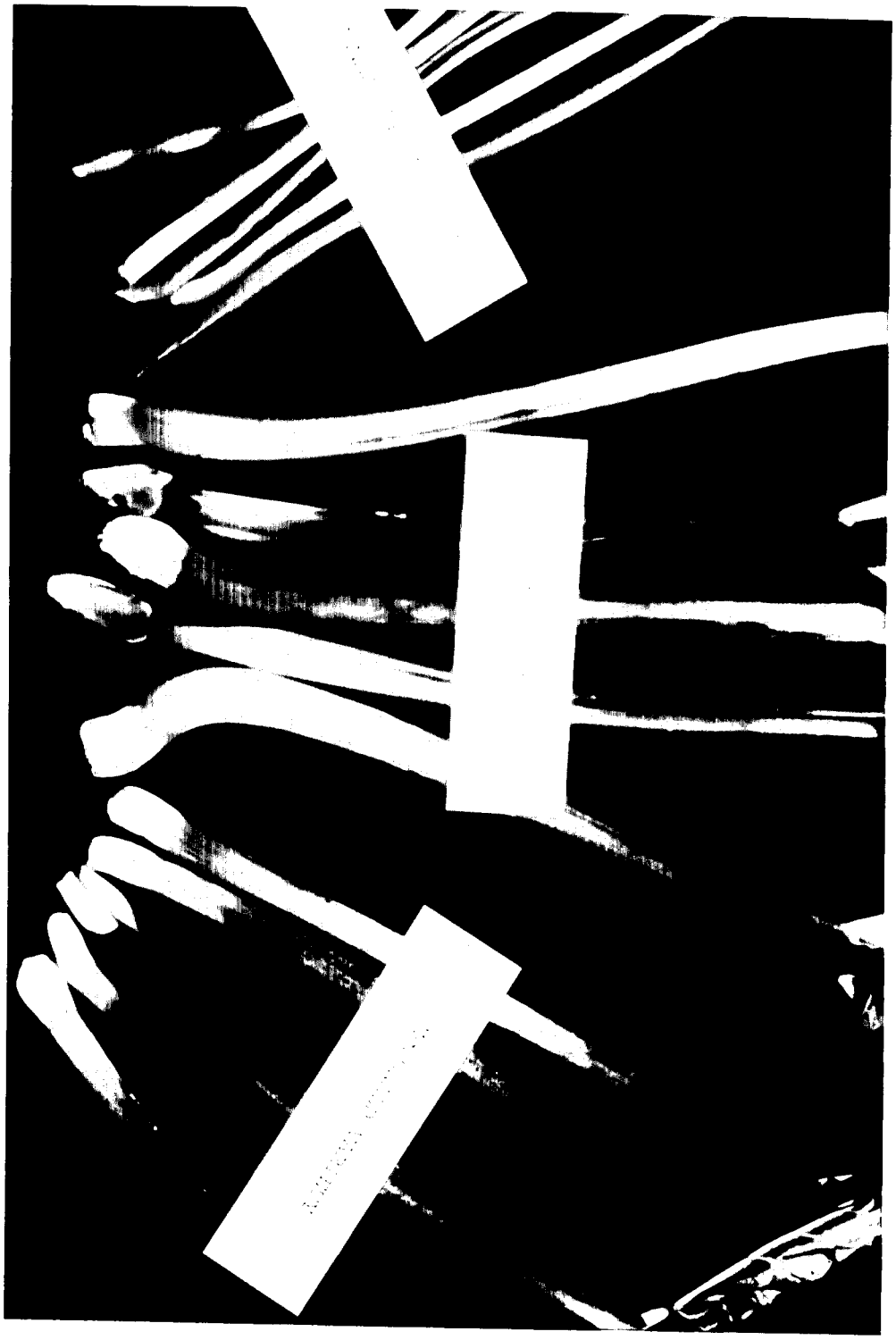

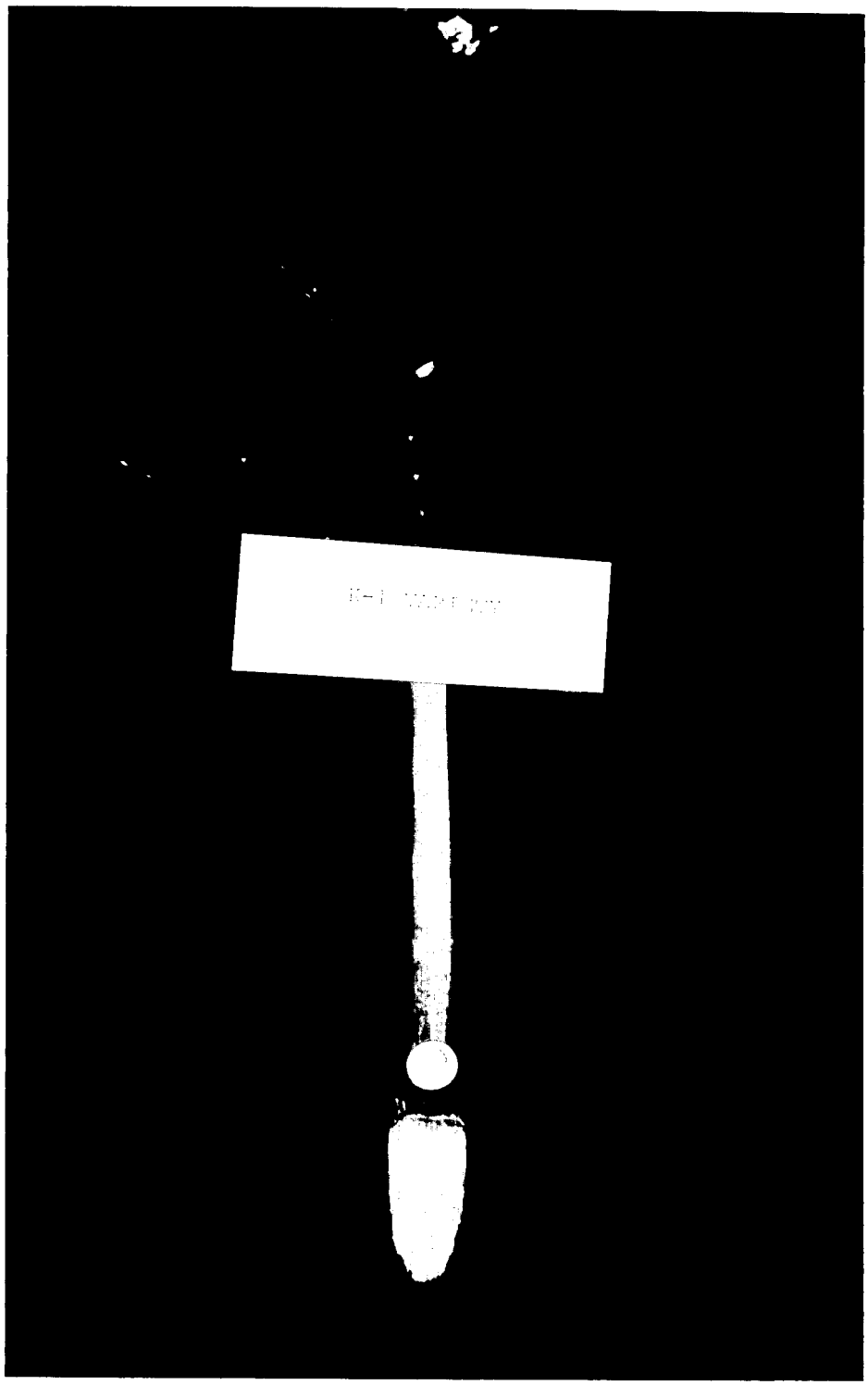

* * * * *